United States Patent [19]

Hanss, deceased et al.

[11] Patent Number: 4,835,457
[45] Date of Patent: May 30, 1989

[54] APPARATUS AND PROCESS FOR DETERMINING THE DEFORMABILITY OF THE RED CORPUSCLES IN THE BLOOD

[75] Inventors: Maxime F. Hanss, deceased, late of Saint-Witz; R. Guillet, Paris; D. Vassauk, Poissy, all of France; Evelyne A. M. Delatour, legal representative, Saint Witz; Michel M. L. Hanss, legal representative, Venissieux; Françoise M. N. Hanss, legal representative, Paris; Thierry M. L. Hanss, legal representative, Lyons; Géraldine B. N. Hanss, legal representative, Saint Cloud, all of France

[73] Assignee: Université René Descartes, Paris, France

[21] Appl. No.: 136,532

[22] Filed: Dec. 22, 1987

Related U.S. Application Data

[63] Continuation of Ser. No. 768,226, Aug. 22, 1985, abandoned.

[30] Foreign Application Priority Data

Aug. 24, 1984 [FR] France ............... 84 13171

[51] Int. Cl.⁴ ..................................... G01N 27/00
[52] U.S. Cl. ..................... 324/71.4; 324/71.1
[58] Field of Search ............... 324/71.1, 71.4; 73/61.4; 377/10-12; 128/632, 635, 637, 734, 774

[56] References Cited

U.S. PATENT DOCUMENTS

| | | | |
|---|---|---|---|
| 3,815,022 | 6/1974 | Golibersuch | 324/71.1 |
| 4,055,799 | 10/1977 | Coster et al. | 324/71.1 |
| 4,348,890 | 9/1982 | Hanss | 73/61.4 |
| 4,521,729 | 6/1985 | Kiesewetter et al. | 324/71.1 |

OTHER PUBLICATIONS

A Method for the Measurement of the Red Blood Cell Deformability Scand J. Clin, Lab. Inves., 41, Suppl. 156, 1981, pp. 229-232.
Clinical Aspects of Blood Viscosity and Cell Deformability, Springer-Verlag, Berlin Heidelberg, New York, 1987, pp. 1-26.

*Primary Examiner*—Reinhard J. Eisenzopf
*Assistant Examiner*—Jack B. Harvey
*Attorney, Agent, or Firm*—Oblon, Fisher, Spivak, McClelland & Maier

[57] ABSTRACT

An apparatus for the measurement of the red blood cell deformability having a measurement cell formed of two electrically insulated compartments clamped mechanically one against the other, with a commercially available multipore membrane therebetween, each of the parts having inlet and outlet orifices as well as a cavity having one electrode and a lateral hole. One of the cavities contains a buffer, the other being intended to receive a suspension of red blood cells consisting of a dilution of a small volume of red blood cells in a large volume of an isotonic conducting buffer, having a volume concentration allowing substantially the transit of a single red blood cell at a time through the multipore membrane, under the action of a device for applying pressure connected to the cavity containing the suspension. An electronic device translates into transit times the electric impedance variations corresponding to the transit of each single red blood cell through the multipore membrane.

5 Claims, 3 Drawing Sheets time scale horizontal axis : 0,4ms/mm

APPARATUS AND PROCESS FOR DETERMINING THE DEFORMABILITY OF THE RED CORPUSCLES IN THE BLOOD

This application is a Continuation Div. of application Ser. No. 768,226, filed on Aug. 22, 1985, now abandoned.

BACKGROUND OF THE INVENTION

1. Field of the Invention

The present invention relates to an apparatus and process for determining the deformability of red corpuscles in the blood.

The red corpuscle which has a diameter of about 7.5 microns, has the form of a disk whose section is that of a biconcave lens. This form, particularly adapted to gas exchanges, contributes to the elasticity and deformability of the red corpuscle, which are required for its tubulent journey through blood flow ducts and more particularly in capillaries some of which scarcely exceed 2 to 3 microns in diameter, i.e. appreciably less than that of the red corpuscle. The deformability of the red corpuscle is a property which is more and more investigated, not only for fundamental research but for clinical research. Thus, too great a red blood corpuscle rigidity leads to hematological (anemias) and microcirculatory irregularities which in extreme cases may lead to the death of the subject (drepanocytoses). The measurement of the deformability of the red corpuscles is therefore a scientific and clinical necessity.

2. Description of the Prior Art

Nurmerous methods have been proposed and developed i.e. the rigidity of the red corpuscle. These methods may be classed in two categories:

First category called comprehensive methods: the measurement is carried out on the whole of the corpuscle. To this category belong:

filtration methods which are based on the flow of a suspension of red blood corpuscles through calibrated holes of a diameter less than that of the red corpuscles (see more particularly the work of Teitel P. "Blood Cells. 3, 55–70 1977"), of Hanns M.F., French Pat. No. 2 463 927 Biorheology, 20(2)199-212 1983 and still others);

optical diffraction methods which are based on the analysis of the optical diffraction spot of the red corpuscles deformed by a shearing flow (see more particularly Bessis et Al. "Blood Cells" 1. 307-313 1975");

Second category, called individual methods: each measurement is made on an individual and the results are averaged. To this category belong:

the method using the measurement of the deformability by aspiration into a micropipette: the static (aspiration) and dynamic (ejection) deformation of the corpuscle are observed;

the method using the measurement of the transit time through a single pore (see more especially the work of Kiesewetter et al. "Scand. J. Clin. Lab. Invest." 41, Suppl. 156, 229-231 1981" and "Biorheology 19, 737-753 1982").

Each category, each method has its advantages and disadvantages. The comprehensive methods are much simpler but their principle defect is that they cannot reveal a subpopulation and can only give a qualitative idea. The individual methods on the other hand are much more reliable since they give a more exact image and allow the exact percentage to be detected, in other words they allow the number of rigid corpuscles to be quantified. However the individual methods are economically very expensive, and are difficult and long to carry out: For example Kiesewetter et al. (above mentioned references) use a membrane containing a single hole of the passage of the corpuscle. The times taken by the filtration experiment are extremely long, there is frequent clogging and the membranes are expensive.

The purpose of the present invention is then to provide an apparatus and a method for measuring the deformability of red corpuscles, which answer better the requirements of practice and the methods and devices known heretofore, more especially in that they are both easy to use and combine the comprehensiveness of the first category with the accuracy and reliability of the second category.

SUMMARY OF THE INVENTION

The present invention provides an apparatus for determining the deformability of the red blood corpuscles using a filtration method and measuring the transit time of the corpuscle by means of electric impedance variations, which apparatus comprises in combination:

a measurement cell formed from two electrically insulated parts, or compartments (for example made from a plastic material), clamped mechanically one against the other, each of these parts comprising input and output orifices as well as a cavity having a lateral hole, one of the cavities containing a buffer, the other being intended to receive the suspension to be measured;

a vertical filter holder clamped between the two parts of the measurement cell at the very position of the two lateral holes;

a vertically mounted filter formed by a commercially available membrane made from a plastic material, of a thickness of the order of 3 to 20 microns having pores whose diameter is between 3 and 5 microns, said membrane being obstructed by a mask over the major part thereof so as to leave only a small and limited number of pores, of the order of 15 to 100 pores, open to the flow;

two electrodes, one in each of said cavities placed at the height of the filter holder opposite the filter;

an electronic device for translating the electric impedance variation into the transit time of the corpuscles.

Thus, instead of using very expensive membranes such as those described by Kiesewetter, a simple commercially available membrane is used, for example the polycarbonated membrane commercialized by NUCLEPORE, with a hold density close to $4.10^5$ per $cm^2$, but practically all the holes of which—except for 15 to 100-have been obstructed by a mask. The vertical position of the filter also reduces clogging.

In a particularly advantageous embodiment of the device of the present invention, the mask is formed by an electrically insulating film, possibly adhesive, pierced with a hole 10 to 500 microns in diameter.

Thus a filter is obtained at will with perfectly defined and accurate holes, for the dispersion of the characteristics of the holes of a membrane of the NUCLEPORE type is very small for adjacent holes.

In another advantageous embodiment of the device of the present invention, the upper orifice of the part of the measurement cell containing the suspension is connected to a system for applying pressure.

In accordance with the invention, the electrodes are formed by stainless steel needles connected to syringes for introducing the buffer and the suspension to be measured, respectively.

The electrodes allow a voltage to be applied proprtional to the resistance of the filter. This voltage is obtained by means of a current of constant intensity passing through the cell.

During the whole time corresponding to the passage of a red corpuscle through a pore, the electric resistance of the membrane is increased, for the red blood corpuscles are substantially electrically insulating, compared with the buffers used which are very conducting. The result is an electric pulse of a duration substantially equal to that of the passage of the red corpuscles through the filter. This duration is called transit time of the red corpuscles. It follows that the greater the rigidity of the red corpuscle (so less deformable and passing with difficulty through the pores), the longer is the corresponding pulse. In other words, if for example a rigid red blood corpuscle follows a normal red blood corpuscle (so readily deformable), a pulse of long duration is observed following a pulse of short duration.

In an advanageous embodiment of the present invention the electronic device is connected to a signal processing device and to a recorder.

Thus a very accurate histogram is obtained which corresponds perfectly to the distribution of the rheological properties of the red corpuscles investigated.

The present invention also relates to a method for measuring the deformability of the red blood corpuscles in which:
- a suspension of red blood corpuscles is prepared by diluting a small volume of red corpuscles in a large volume of isotonic conducting buffer, so as to obtain a volume concentration of the order of 0.01 to 1%;
- the two cavities of the measurement cell are filled respectively with pure buffer and the suspension obtained by means of two needles;
- the flow of the suspension is established through the membrane by applying a desired over pressure in the compartment containing the suspension, the electrodes and the recording apparatus being switched on, and,
- the histogram of the transit times corresponding to the measured suspension is plotted.

Apart from the above arrangements, the invention comprises other arrangements which will be clear from the following description.

The invention will be better understood from the description which follows with reference to an embodiment of the apparatus of the present invention shown in the accompanying drawings, as well as an example of measuring the deformability of red corpuscles.

It should however be understood that the device as described in what follows and as shown in the drawings, as well as the example of putting the process into practice in accordance with the present invention, are given solely by way of illustration of the invention and form in no ways a limitation thereof.

BRIEF DESCRIPTION OF THE DRAWINGS

The apparatus according to the present invention, which determines the deformability of the red blood corpuscles will now be described with reference to the accompanying drawings, in which.

DESCRIPTION OF THE PREFERRED EMBODIMENT

Figure 1:
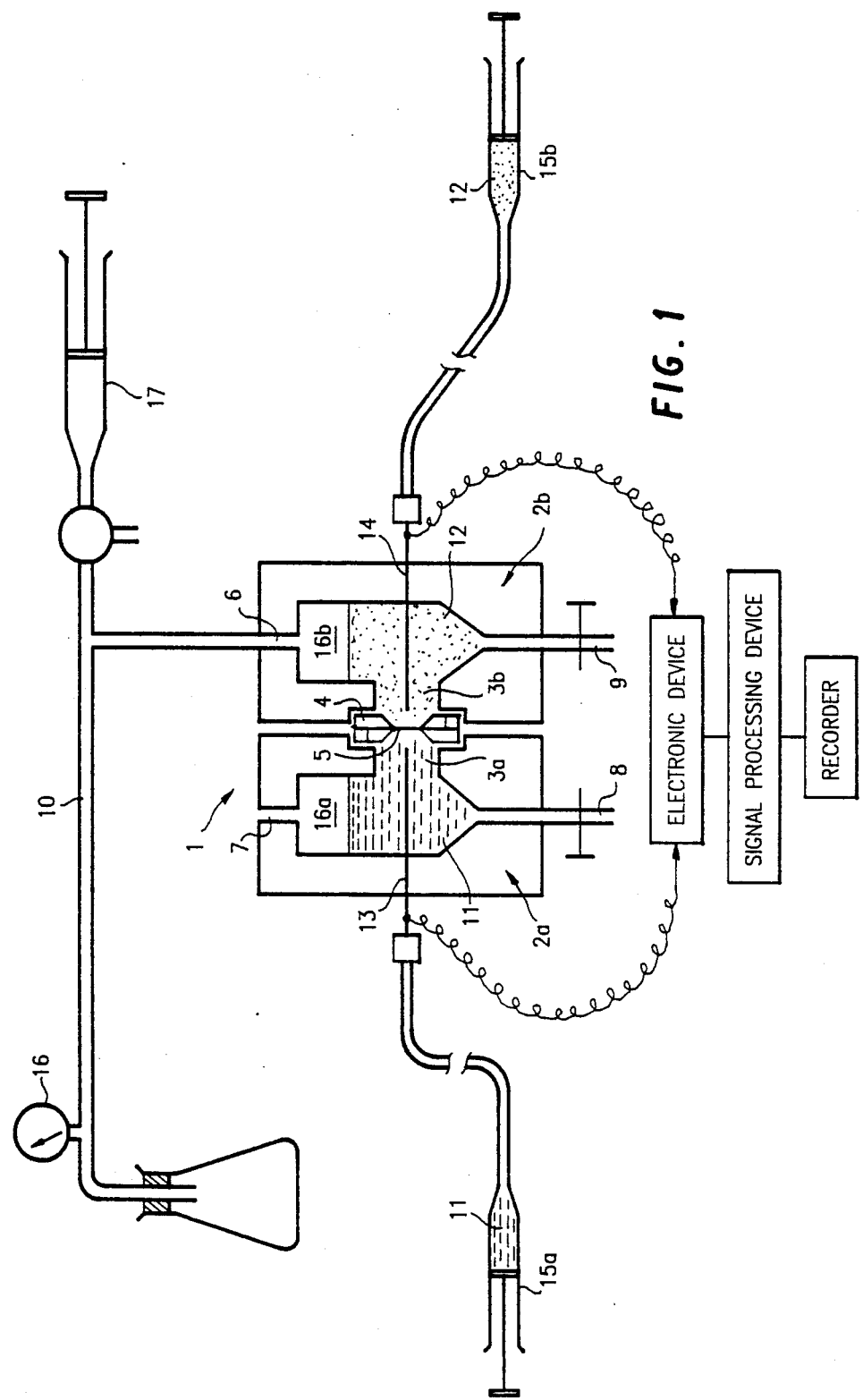
FIG. 1 shows schematically the whole of the apparatus: the two parts of the measurement cell, the electrode needles, the pressurizing device and the filter holder provided with the filtering membrane.

The apparatus for measuring the deformability of the red corpuscles shown in FIG. 1 is formed of a measurement cell 1 having two parts or compartments made from a plastic material 2a and 2b, one (2a) is intended to receive the buffer 11 and the other (2b) the suspension 12 of red corpuscles to be measured. Each of these parts, which are clamped one against the other, comprises a cavity (16a and 16b) provided with a lateral hole (3a and 3b) at the position where the two compartments 2a and 2b clamp therebetween the vertical filter holder 4 which is provided with the filtering membrane 5 closed over the major part thereof by a mask. The two parts 2a and 2b of the measurement cell are provided with orifices 6, 7, 8 and 9; orifice 6 connects the measurement cell to a pressurizing device 10, which device controls and activates the flow of the suspension 12 to be measured towards the buffer 11. Orifice 7 connects part 2a of the measurement cell 1 to the atmospheric pressure, whereas the orifices 8 and 9 serve for draining the buffer 11 and suspension 12, respectively. Electrodes 13 and 14 plunge respectively into the buffer 11 and the suspension to be measured 12. These electrodes are formed by stainless steel needles, which needles are connected to syringes 15a and 15b and also serve for supplying the measurement cell with buffer 11 (electrode needle 15a) and with suspension 12 (electrode needle 15b).

The pressure gauge 16 allows the pressure exerted in compartment 2b to be measured. This pressure is created by means of a simple device, for example, a bulb or a syringe 17.

Needle 14 which corresponds to the suspension also allows filter 5 to be unclogged if required by adding a small amount of suspension, thus causing a slight local over pressure, sufficient for removing the particles clogging the pores, such as red blood corpuscle aggregates, possibly white corpuscles, etc.

Figure 2:
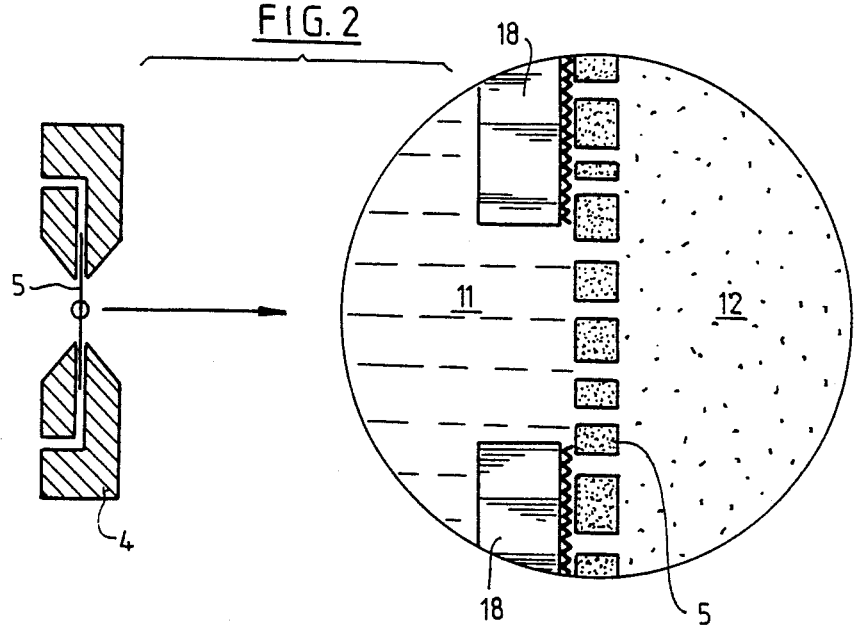
FIG. 2 shows the detail of the filter (filter holder + membrane)

FIG. 2 shows the detail of the filter holder provided with the filtering membrane 5. This latter is closed over the major part thereof by the electrically insulating ribbon 18 which only leaves free a very limited number of pores; about 15 to 100.

Figure 3:
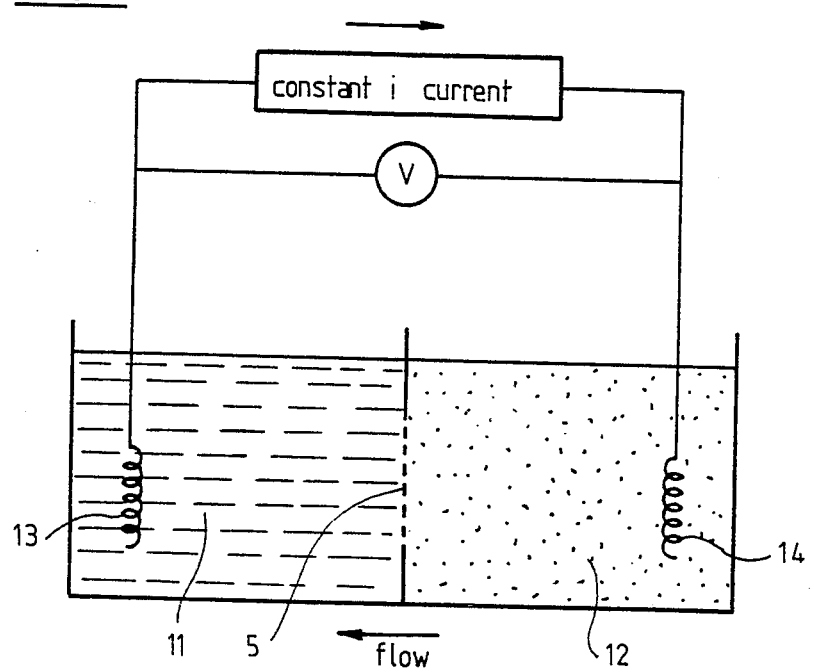
FIG. 3 shows the detail of the filtering membrane.
Figure 4:
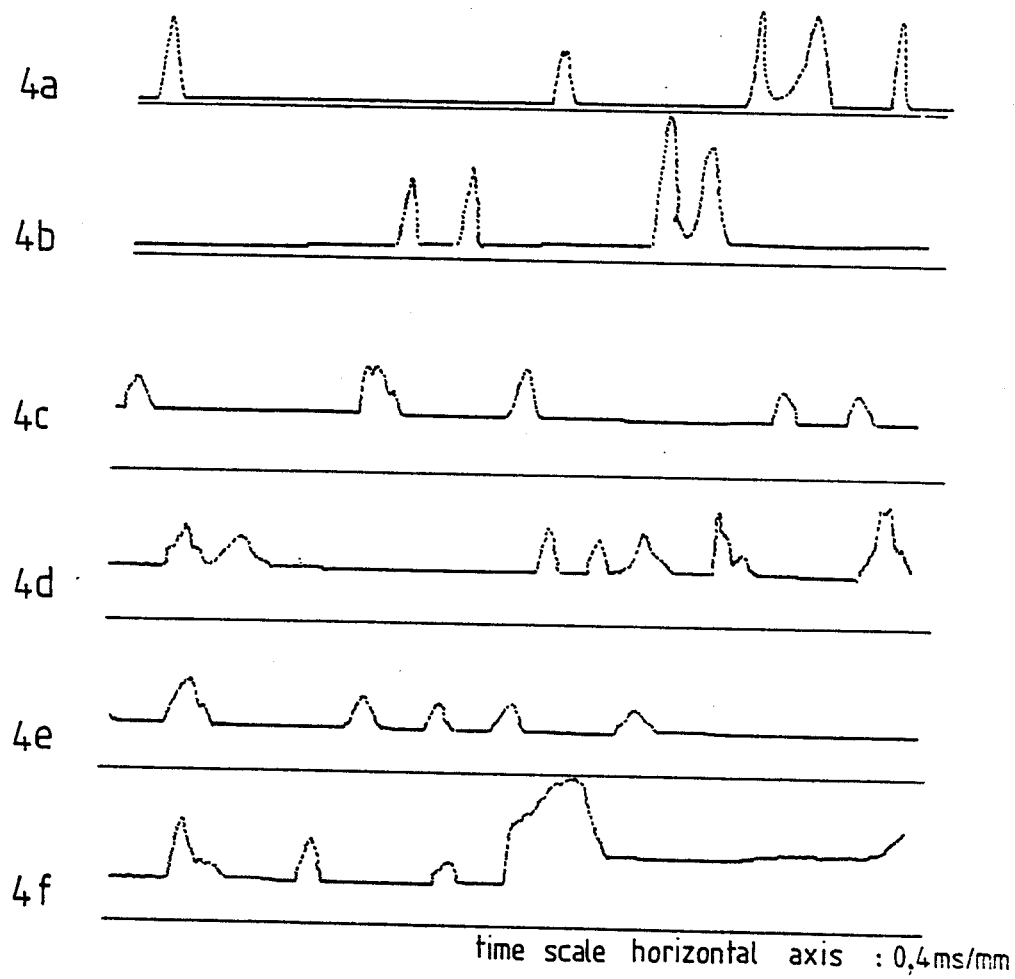
FIG. 4 shows examples of recordings obtained.

The suspension 12 flows through the filtering membrane 5 towards the compartment 3a containing the buffer 11 (FIG. 3), electrodes 13 and 14 are placed at the height of the membrane 5. The variations of the electric resistance of filter 5 depend on the presence of red corpuscles in the pores: with a constant electric bias, the current and so the electric resistance is measured. The concentration of suspension 12, the pressure (obtained by device 10), the number of holes in membrane 5 are chosen so as to optimize the measurement; passage of a single corpuscle at a time. A conventional electronic device and a simple data processing tool not specific to the handling (not shown in the accompanying drawings) allow the electric impedance variations to be translated into transit lines, the pulses obtained to be displayed (FIG. 4), and histograms to be obtained corresponding to the distribution of the rheological properties of the red blood corpuscles investigated.

A non-limiting example will be given hereinafter of measurement of the deformability of the red blood corpuscles in accordance with the process of the present invention.

Measurement Example

The filtering membrane which is used is, for example, the polycarbonated membrane commercialized by NUCLEPORE of a thickness of 11 microns, containing $4.10^5$ pores per $cm^2$, whose average diameter is about 5 microns. On this membrane is bonded an adhesive ribbon (of trademrk 3M for example) in a sufficient amount to leave only about 20 to 50 pores; the mask formed by this adhesive film is pierced with a hole of a diameter of 175 microns for example. The membrane thus formed is then mounted in the vertical filter holder. Then the two cavities of the two compartments of the measurement cell are filled using the electrode needles connected to syringes; one cavity is filled with buffer Tris-HCl with pH=7.4, the other with the suspension to be measured, of a volume concentration (hematrocrit Ht) of the order of 0.0% to 1%, for example 0.1%. The value of this concentration depends on the number of effective pores and on its characteristics. It is desirable to have a single corpuscle passing at a time, as quickly as possible.

The red blood corpuscle susspension is prepared by diluting a small volume of red corpuscles in a large volume of isotonic conducting buffer. To obtain flow of the red blood corpuscles through the filtering membrane, a desired over pressure is applied of the order of 1 to 100 mm of water, for example 50 mm of water by means of a device 10 connected to a compartment containing the suspension to be measured.

FIGS. 4a and 4b show the pulses obtained during passage of the normal red corpouscles. FIGS. 4c, 4d, 4e and 4f show the pulses obtained during the passage of red blood corpuscles of a pathological blood (drepanocytosis): the presence of short duration pulses will be noted corresponding to normal corpuscles and long duration pulses and of a different shape corresponding to the rigid corpuscles.

As is clear from the foregoing, the invention is in no way limited to those of its modes of implementation, embodiments and modes of application which have just been described more explicity; it embraces on the contrary all variants thereof which may occur to a man skilled in the art, without departing from the scope or spirit of the present invention.

What is claimed is:

1. An apparatus for the measurement of red blood cell deformability, of the type using a filtration method and measuring the transit time of the red blood cells by means of electric impedance variations comprising in combination:
    a measurement cell formed of two electrically insulated parts clamped mechanically one against the other, wherein each of said parts comprises:
    inlet and outlet orifices;
    a cavity having a lateral hole,
    wherein one of said cavities contains a buffer, with the other of said cavities being intended to receive a suspension of red blood cells the deformability of which is to be measured;
    a vertical filter holder clamped between the two parts of the measurement cell at the position of the two lateral holes;
    a vertically mounted filter formed by a membrane made from a plastic material of a thickness of the order of 3 to 20 $\mu$m, said membrane comprising a plurality of pores whose diameters are between 3 and 5 $\mu$m, through which the red blood cells are intended to transmit under the action of a device for applying pressure which is connected to the cavity containing the suspension through the corresponding inlet orifice and which creates in this cavity a sufficient pressure with respect to the cavity containing said buffer;
    two electrodes, one in each of said cavities placed at the height of the filter holder opposite said filter;
    wherein the suspension comprises a dilution of a small volume of red blood cells in a large volume of an isotonic conducting buffer, having a volume concentration allowing the transit of substantially a single red blood cell at a time through said multipore membrane under said pressure for a given number of pores;
    an electronic device for translating into transit times the electric impedance variations corresponding to the transit of each single red blood cell through said multipore membrane;
    a signal processing device and a recorder connected to said electronic device.

2. Apparatus as claimed in claim 1, wherein the volume concentration of the red blood cell suspension is on the order of 0.01% to, 0.1% and wherein said pressure is on the order of 100 mm to 10 mm of water and wherein said number of pores is respectively on the order of 100 to 15 pores.

3. The apparatus as claimed in claim 1, wherein said electrodes are formed by stainless steel needles connected to syringes which allow said buffer and said suspension to be introduced in said cavities.

4. A process for the measurement of the red blood cell deformability, of the type using a filtration method and measuring the trnasit time of the red blood cells by means of electric impedance variations, comprising:
    preparing a suspension of red blood cells by diluting a small volume of red blood cells in a large volume of an isotonic conducting buffer;
    filling a first cavity of a measurement cell with a pure buffer and a second cavity of the measurement cell with said suspension,
    placing in said first and second cavities a first and a second electrodes,
    placing said cavities in turn, respectively, in a first and a second compartments of said measurement cell which are electrically insulated and mechanically clamped one against the other,
    placing a filter therebetween formed of a multipore membrane made from a plastic material of a thickness of the order of 3 to 20 $\mu$m and having pores whose diameters are between 3 and 5 $\mu$m, the volume concentration of said suspension being such that there is substantially a single red blood cell at a time that transits through said multipore membrane;
    applying a sufficient pressure in the cavity containing said suspension in order that, under this pressre and with said volume concentration, there is the transit of substantially a single red blood cell through said multipore membrane;

connecting said electrodes to an electronic device for translating the electric impedance variations corresponding to the transit of each single red blood cell through said multipore membrane into transit times;

connecting said electronic device to a signal processing device and to a recorder device;

switching on said electronic, processing and recorder devices and plotting a histogram of the said transit times.

5. Process according to claim 4, wherein the volume concentration of the red blood cell suspension is on the order of 0.01% to 0.1%, and wherein said overpressure is on the order of 100 mm to 10 mm of water and wherein said number of pores is respectively on the order of 100 to 15 pores.

* * * * *